United States Patent [19]

Roberts

[11] Patent Number: 5,244,680
[45] Date of Patent: Sep. 14, 1993

[54] BIOCONTROL OF POSTHARVEST ROTS IN FRUIT

[75] Inventor: Rodney G. Roberts, Cashmere, Wash.

[73] Assignee: The United States of America as represented by the Secretary of Agriculture, Washington, D.C.

[21] Appl. No.: 914,233

[22] Filed: Jul. 13, 1992

Related U.S. Application Data

[63] Continuation of Ser. No. 501,913, Mar. 30, 1990, abandoned.

[51] Int. Cl.$^5$ .................... A01N 63/00; A01N 63/04; C12N 1/14; C12N 1/16
[52] U.S. Cl. ................................ 424/93 S; 424/93 Q; 435/911; 435/255.3
[58] Field of Search .......................... 424/93 Q, 93 S; 435/254, 255, 911

[56] References Cited

U.S. PATENT DOCUMENTS

| | | | |
|---|---|---|---|
| 4,764,371 | 8/1988 | Pusey et al. | 424/93 |
| 4,950,472 | 8/1990 | Janisiewicz | 424/93 |
| 4,975,277 | 12/1990 | Janisiewicz et al. | 424/93 |

OTHER PUBLICATIONS

C. G. Gueldner et al., *Journal of Agricultural and Food Chemistry* 36: 366–370 (1988).
W. J. Janisiewicz, *Phytopathology* 78: 194–198 (1988).
W. J. Janisiewicz and J. Roitman, *Phytopathology,* 78: 1697–1700 (1988).
P. L. Pusey and C. L. Wilson, *Plant Disease* 68: 753–756 (1984).
P. L. Pusey et al., *Plant Disease* 70: 587–590 (1986).
P. L. Pusey et al., *Plant Disease* 72: 622–626 (1988).
A. Tronsmo and J. Raa, *Phytopath. Z.* 89: 216–220 (1977).
R. S. Utkhede and P. L. Sholberg, *Canadian Journal of Microbiology* 32: 963–967 (1986).
Janisiewicz, W. J., Phytopathology, vol. 77, No. 3 (1987) pp. 481–485.
ATCC Catalogue of Fungi/Yeasts (1987), pp. 122–126.

*Primary Examiner*—Douglas W. Robinson
*Assistant Examiner*—Susan M. Weber
*Attorney, Agent, or Firm*—M. Howard Silverstein; John D. Fado; Margaret A. Connor

[57] ABSTRACT

Strains of microorganisms including strains of Cryptococcus are described which have the ability to control postharvest wound or surface fruit pathogens, even at the low temperatures at which fruit is stored. The strains are highly effective in controlling postharvest diseases including mucor rot, blue mold, and gray mold in fruit.

3 Claims, 3 Drawing Sheets

BIOCONTROL OF POSTHARVEST ROTS IN FRUIT

This application is a continuation of application Ser. No. 07/501,913, filed Mar. 30, 1990, now abandoned.

BACKGROUND OF THE INVENTION

1. Field of the Invention

The present invention relates to the biological control of postharvest diseases in agricultural commodities. More particularly, this invention relates to the use of selected strains of microorganisms to biologically control postharvest diseases including mucor rot, gray mold, and blue mold in fruit.

2. Description of the Art

Fruit damage caused by fungi-induced postharavest diseases results in considerable economic losses to the fruit industry worldwide. Some of the most important postharvest diseases of fruit are mucor rot, caused by Mucor spp., blue mold cased by *Penicillium expansum*, and gray mold caused by *Botrytis cinerea*.

Mucor spp., primarily *Mucor piriformis*, the causal fungus of mucor rot, survives in the soil and on rotting fruit in contact with the soil. During harvest, fruit are placed into large wooden bins which rest on the ground. During handling and loading, orchard soil, carrying spores of the fungus, adheres to the bin skids. Fruit become inoculated with the fungus when the bins, along with adhering soil, are placed in immersion dumpers in fruit packinghouses to float the fruit out of the bins and into the processing flumes, and the soil carrying the spores is released into the flume or dumper water. When the spores enter wounds in the fruit they germinate and grow. During growth, the fungus secretes enzymes that break down the fruit tissues, causing them to become soft, watery, and discolored. Currently, there are no postharvest fungicides that give control of this fungus.

Gray mold and blue mold are also major postharvest diseases of fruit and are primarily storage diseases. Traditional attempts to control postharvest diseases include the treatment of the commodity, after harvest and before storage, with a fungicide, for example, benomyl. However, increasing numbers of fungicide-tolerant strains of pathogens associated with postharvest diseases, as well as public concern about pesticide residues on food products, has stimulated efforts to develop alternative systems of disease control for agricultural products. In the case of mucor rot, a further incentive is that no chemical control treatment is available, because fungicides, e.g., benomyl, do not effect Mucor spp.

One alternative is the use of biological agents to control postharvest diseases. Postharvest biological control systems for fruit have been actively investigated for the past decade. These include iturins as anitfungal peptides in biological control of peach brown rot with *Bacillus subtilis*(C. G. Gueldner et al., *Journal of Agricultural and Food Chemistry* 36: 366–370 (1988)); postharvest control of blue mold on apples using *Pseudomonas* spp. isolate L-22-64 or white yeast isolate F-43-31 ( W. J. Janisiewicz, *Phytopathology* 77: 481–485 (1987)); biocontrol of blue mold and gray mold on apples using an antagonistic mixture of *Pseudomonas* sp. and *Acremonium breve* (W. J. Janisiewicz, *Phytopathology* 78: 194–198 (1988)); control of gray mold and reduction in blue mold on apples and pears with an isolate of *Pseudomonas capacia* and pyrrolnitrin produced therefrom (W. J. Janisiewicz and J. Roitman, *Phytopathology* 78: 1697–1700 (1988)); postharvest control of brown rot in peaches and other stone fruit with the B-3 strain of *Bacillus subtilis* (P. L. Pusey and C. L. Wilson, *Plant Disease* 68: 753–756 (1984); P. L. Pusey et al., *Plant Disease* 70: 587–590 (1986), P. L. Pusey et al., *Plant Disease* 72: 622–626 (1988), and U.S. Pat. No. 4,764,371 to Pusey et al.); antagonistic action of *Trichoderma pseudokoningii* against *Botrytis cinerea Pers.* which causes the dry eye rot disease of apple (A. Tronsmo and J. Raa, *Phytopath. Z.* 89: 216–220 (1977)), and postharvest control of brown rot and alternaria rot in cherries by isolates of *Bacillus subtilis* and *Enterobacter aerogenes* (R. S. Utkhede and P. L. Sholberg, *Canadian Journal of Microbiology* 32: 963–967 (1986)). Presently, there are no postharvest biocontrol systems in widespread commercial use.

SUMMARY OF THE INVENTION

I have discovered a method for selection of microorganism strains which have the ability to inhibit the growth of postharvest pathogens on fruit. In one embodiment, microorganisms are selected that have the ability to control postharvest fruit pathogens at the low temperatures at which fruit is stored. In another embodiment, strains of Crytococcus are selected to biologically control postharvest diseases.

Microorganism strains selected by my methods are highly effective in controlling postharvest diseases including mucor rot, blue mold, and gray mold.

A method for biologically controlling or inhibiting postharvest rots in fruit using the strains is disclosed. In brief, the method comprises treating a fruit with the selected strain in an amount effective to inhibit the development of the target pathogen.

Compositions of the strains in combination with an agriculturally acceptable carrier are encompassed by the invention.

In contrast to previously known bacterial biocontrol agents, the microorganism strains selected in accordance with the method of the first embodiment are distinct from other postharvest biocontrol agents in that they have the ability to effectively control postharvest decay at low temperatures and proliferate in wounds and on the surface of fruit at low temperatures. They are unique in that they have demonstrated physiological adaptation to both wound environment (ability to proliferate in wounds) and to cold temperatures of postharvest storage (ability to prosper at low temperatures (psychrophilia). This is of critical importance because fruit are stored at low temperatures, often as low as 0° C. Several postharvest fruit pathogens, including several species of Penicillium and *Botrytis cinerea* and Mucor spp. can germinate and grow at low temperatures, even as low as 5° C. All the biological antagonists cited above, except Trichoderma (Tronsmo and Raa, supra) were conducted at warm temperatures because of the growth requirements of the antagonists themselves. Efficacy of Trichoderma was studied at low temperature, but was not effective. Pusey et al., 1986, supra, studied biocontrol of *B. subtilis* strain B-3 under simulated cold storage conditions (2°–4° C. and 70-100% Relative Humidity). However, the researchers did not inoculate the fruit with the pathogen until the fruit was removed from cold storage, and incubation was at 20° C., biasing the results.

The method of the second embodiment selects strains of Cryptococcus for use as biocontrol agents. This is the first report of strains of Cryptococcus yeast having the ability to control postharvest diseases in fruit. Test data on Cryptococcus strains obtained by the method demonstrate that they are highly effective in controlling postharvest diseases on fruit. Additionally, the Cryptococcus strains have demonstrated compatibility with other postharvest chemicals such as fungicides and antioxidants. Thus, the strains can be used in combination with these chemicals to simultaneously control postharvest rots and other pathogens, e.g., ascomycetous fungal pathogens. The Cryptococcus strains I have obtained by my method also differ from the prior art biocontrol agents described above in that control of postharvest fungal decay was obtained without the production of fungitoxic extracellular antibiotics. All of the prior art bacterial antagonists described above require conditions of growth to allow production of toxic extracellular antifungal metabolites, either in the culture medium or in wounds, before the materials are effective. Not only does the necessity for the presence of these metabolites pose a potential health risk which has not been evaluated, but may limit their effectiveness when used under the variety of circumstances encountered in commercial situations.

In sum, the strains of the invention overcome the disadvantages of the previously known postharvest biological control agents in that they can prosper and give biological control of postharvest decays in wounds in fruit at the low temperatures at which fruit are stored. Further, selected strains can control postharvest fungal decay without the production of fungitoxic extracellular antibiotics.

The use of the strains of the invention for postharvest biocontrol of fungal decay also has the advantage over conventional chemical control methods in that there are no pesticide residues in the fruit associated with postharvest application of fungicides. When strains of Cryptococcus are used for disease control, there are no chemicals or foreign microorganisms present on the fruit after application that are not naturally resident since yeast strains are naturally present on fruit.

In accordance with this discovery, it is an object of this invention to provide strains of microorganisms having the ability to proliferate in wounds and on the surface of fruit at low temperatures for use as biological control agents to control postharvest wound or surface fruit pathogens. It is a further object of the invention to provide strains of Cryptococcus for use as biocontrol agents. The strains of the invention are highly effective in controlling postharvest diseases including mucor rot, blue mold, and gray mold in fruit. Methods for selecting the strains are disclosed.

A further object of the invention is the provision of compositions comprising the strains and an agricultural carrier to control postharvest diseases in fruit.

It is also an object of the invention to provide a means for biologically controlling postharvest diseases in fruit using the strains.

Still another object of the invention is to provide a method for simultaneously controlling two or more pathogens causing postharvest diseases in fruit.

Other objects and advantages of this invention will become readily apparent from the ensuing description.

DETAILED DESCRIPTION OF THE DRAWINGS

FIG. 1 shows the effect of temperature on growth of *Cryptococcus laurentii* NRRL Y-18623 in wounds of cultivar Golden Delicious apple fruit. Data are from one trial, points represent mean colony counts from three replicate fruit, each plated in triplicate at each sampling time for each temperature. Bars represent standard error of the mean.

DETAILED DESCRIPTION OF THE INVENTION

Figure 1:
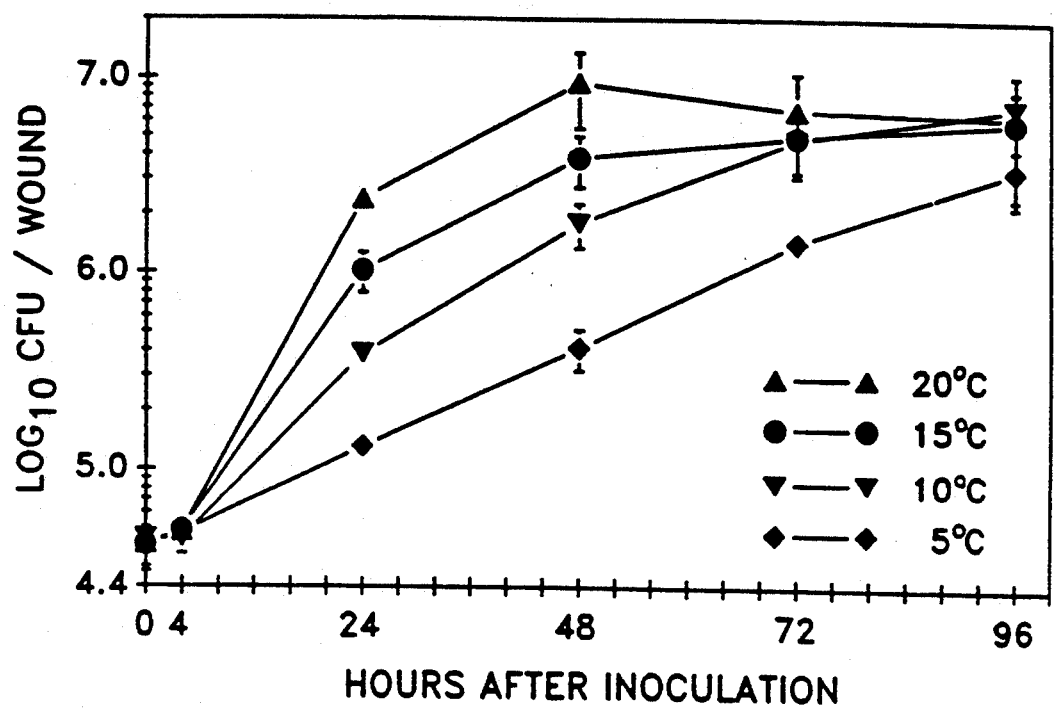

Three hundred isolates of bacteria and yeasts were isolated from the external surfaces of twigs, leaves, and fruits of pears, apples, and cherries. One hundred twenty five of the isolates were bioassayed for antagonistic activity against *Penicillium expansum, Penicillium viridicatum, Alternaria alternata, Botrytis cinerea*, and Mucor sp. as described in detail in Example 1, below. One strain, identified as *Cryptococcus laurentii* NRRL Y-18623, controlled gray mold lesion development caused by *B. cinerea*. The rapid growth of the Cryptococcus strain in wounds over a wide range of temperatures, especially cold temperatures, and its ability to control lesion development by Botrytis shows that the Cryptococcus strain is well adapted to the wound environment in fruit (Example 2, below). Further, studies showed that the strain can proliferate in wounds in fruit under low oxygen conditions, as low as 1½% $O_2$ and when $CO_2$ was raised to 2% (conditions which occur under controlled atmosphere storage conditions). The strain also controlled blue mold caused by *Penicillium expansum*. This is the first Cryptococcus strain reported having the ability ot control postharvest diseases in fruit.

Taxonomic characteristics of *C. laurentii* (Kufferath) Skinner NRRL Y-18623 are as follows:

Colonies were buff/cream, mucoid, with budding, and lacking filaments, ballistoconidia and asci. Colonies from 3-day-old stationary cultures in YM Broth (Kreger-van RiJ, *The Yeasts*, Elsevier Science Publishers B.V., Amsterdam, The Netherlands (1987)) showed the following characteristics: sediment flocculent, moderate, islets absent. Cells single, double, or in short chains of 3–4 cells. Cells broadly ellipsoidal to ellipsoidal, multilateral budding. Bud scar initially narrow, becoming rather broad and developing a distinct collarette with successive budding. Cell measurements and length/width ratios are presented in Table 1.

| Fermentation of sugars: | − | | |
|---|---|---|---|
| Nitrate assimilation: | − | | |
| Growth | | | |
| at 37° C. | − | | |
| at 25° C. | + | | |
| Assimilation of carbon compounds: | | | |
| D-glucose | + | Raffinose | + |
| D-galactose | + | Melezitose | + |
| L-sorbose | − | Inulin | − |
| D-glucosamine | + | Soluble starch | − |
| D-ribose | + | Glycerol | − |
| D-xylose | + | Meso erythritol | + |
| L-arabinose | + | Ribitol | + |
| D-arabinose | + | Xylitol | + |
| L-rhamnose | + | L-arabinitol | − |
| Sucrose | + | D-glucitol | + |
| Maltose | + | D-mannitol | + |

-continued

| | | | |
|---|---|---|---|
| Trehalose | + | Galactitol | − |
| Methyl α-glucoside | + | Myo-inositol | + |
| Cellobiose | + | Glucono δ-lactone | + |
| Salicin | + | D-gluconate | + |
| Arbutin | + | DL-lactate | + |
| Melibiose | + | Succinate | + |
| Lactose | + | Citrate | + |
| Assimilation of other compounds: | | | |
| Ethylamine | + | | |
| L-lysine | + | | |
| Cadaverine | + | | |

A stringent in vivo screening procedure was designed to select yeast strains having the ability to control postharvest diseases in fruit. This procedure provided a rigorous evaluation of biocontrol efficacy, because the strains were challenged with an increased concentration of pathogen and because internal, unobvious lesions were detected. This procedure is described in Example 4, below. It has the following features: (1) Four fruit per yeast/pathogen combination were wounded three times each. (2) Yeast cells were separated from their growth medium by centrifugation and were washed three times with sterile buffer. Suspensions of the washed cells were used in screening bioassays. (3) After visual examination, the fruit were sliced through each wound to determine if decay had developed in internal tissues. (4) The concentrations of pathogen spores was increased so as to ensure vigorous disease development in controls and to provide a more severe challenge to the antagonists.

Strains were screened using this procedure. Six additional basidiomycetous yeast strains were identified as having the ability to control postharvest diseases in fruit: four strains of *Cryptoccocus flavus*, denoted as *C. flavus* NRRL Y-18617, NRRL Y-18618, NRRL Y-18619, and NRRL Y-18620; one strain of *Cryptoccocus albidus*, denoted as *C. albidus* NRRL Y-18621, and one more strain of *Cryptoccocus laurentii*, denoted as *C. laurentii* NRRL Y-18622.

Taxonomic characteristics of the strains are as follows:

Colonies from 3-day-old stationary cultures in YM Broth (Kreger-van Rij, *The Yeasts*, Elsevier Science Publishers B.V., Amsterdam, The Netherlands (1987)) showed the following characteristics:

All *C. flavus* strains: sediment moderate, flocculent, islets absent. Cells oval to ellipsoidal.

*C. albidus* NRRL Y-18621: sediment flocculent, sparse, islets absent. Cells spherical to ellipsoid, generally broadly ellipsoidal, multilateral budding, single, in pairs, or in short chains of 3-4 cells.

*C. laurentii* NRRL Y-18622: sediment flocculent, moderate. Small islets present. Cells single, double, or in short chains of 3-4 cells. Cells broadly ellipsoidal to ellipsoidal, multilateral budding. Bud scar initially narrow, becoming rather broad and developing a distinct collarette with successive budding.

Cell measurements and length/width ratios for the strains are presented in the Table 1. Additional taxonomic data are listed in Table 2.

TABLE 1

| | LENGTH | WIDTH | L/W RATIO |
|---|---|---|---|
| Y-18623 | 4.2–(5.6)–6.6 | 2.7–(3.7)–4.6 | 1.2–(1.5)–2.1 |
| Y-18622 | 4.2–(5.1)–5.9 | 3.2–(3.7)–4.2 | 1.2–(1.4)–1.5 |
| Y-18617 | 3.8–(5.0)–6.0 | 3.5–(4.5)–5.6 | 1.0–(1.1)–1.4 |
| Y-18618 | 4.3–(5.1)–5.8 | 3.9–(4.6)–5.4 | 1.0–(1.1)–1.3 |
| Y-18619 | 3.7–(5.2)–5.8 | 3.6–(4.7)–5.7 | 1.0–(1.1)–1.3 |
| Y-18620 | 4.2–(5.1)–6.1 | 4.0–(4.7)–5.9 | 1.0–(1.1)–1.3 |
| Y-18621 | 4.1–(5.8)–7.0 | 3.6–(4.7)–6.4 | 1.0–(1.2)–1.6 |

TABLE 2

| | Y-18617 | Y-18618 | Y-18619 | Y-18620 | Y-18621 | Y-18622 |
|---|---|---|---|---|---|---|
| Growth on Inositol: | | | | | | |
| Solid | + | + | + | + | + | + |
| Liquid | + | + | + | + | + | + |
| Glucose Fermentation: | | | | | | |
| Gas | − | − | − | − | − | − |
| Acid | +w | +w | +w | +w | − | +w |
| Nitrate Assimulation | − | − | − | − | +w | − |
| Growth at 37° C. | +w | − | − | − | − | − |
| Starch Production | − | − | − | − | − | + |
| Carbohydrate Utilization: | | | | | | |
| Lactose | + | + | + | + | + | + |
| Cellobiose | + | + | + | + | + | + |
| Rhamnose | + | + | + | + | + | + |
| Erythritol | + | + | + | + | − | + |
| Sucrose | + | + | + | + | + | + |
| Maltose | + | + | + | + | + | + |
| Melibiose | + | + | + | + | + | + |
| Melezitose | + | + | + | + | + | + |

Statement of Deposit. Biologically pure cultures of the Cryptococcus strains were deposited under terms of the Budapest Treaty Feb. 14, 1990 in the Agriculture Research Culture Collection (NRRL), Northern Regional Research Center, Agricultural Research Service, U.S. Department of Agriculture, Peoria, Illinois, 60164, and have been assigned the accession numbers as noted above. For purposes of this invention, any isolate or subculture of the deposited strains or combinations of strains are encompassed by the invention.

Selection Method. Other strains of microorganisms, in addition to the deposited strains, for use as biocontrol agents to control postharvest wound or surface fruit pathogens, are obtained by the following in vivo selection methods.

First embodiment: In this method, microrganisms are selected that have the ability to control postharvest fruit pathogens at the low temperatures at which fruit is stored, i.e., about 0°–15° C. The test strain is grown up on a suitable nutrient medium. The cells are separated from the growth medium, e.g., by decanting, centrifugation, and washed to obtain cells substantially free of the growth medium. Next, the cells are suspending in water or buffer, to obtain a suspension having an effective amount of the organism, generally, about $1 \times 10^7$ CFU/ml. The suspension is applied to the surface or wound of the fruit, and the surface or wound is inoculated with the test pathogen in an amount sufficient to cause disease in control fruit (fruit treated the same but without the microorganism treatment). For example, the amount of pathogen that is used to select a strain effective against the following pathogens is as follows: at least $2 \times 10^4$ spores/ml Botrytis spp., at least $1 \times 10^3$ spores/ml Penicillium spp., or $4 \times 10^4$ to $1 \times 10^5$ spores/ml Mucor spp. The fruit is incubated for a sufficient time and at a temperature conducive to causing proliferation of the pathogen on the fruit.

Microorganism strains are selected which effectively inhibit the growth of the pathogen on the fruit. A strain is considered effective when it causes at least a 50% reduction in the number of fruit infected by the pathogen or at least a 50% reduction in the number of wounds infected by the pathogen, when compared to control fruit.

Next, the selected strain is subjected to a second test wherein the microorganism strain is grown on the surface or in the wound of a fruit in the presence of the pathogen at 5°-15° C., preferably 5°-10° C., the pathogen being present in an amount sufficient to cause disease in fruit not treated with the strain (low temperature control). A microorganism strain is selected as one which effectively inhibits the growth of postharvest fruit pathogen at low temperatures if it causes at least a 50% reduction in the number of fruit infected by the pathogen or at least a 50% reduction in the number of wounds infected by the pathogen, when compared to low temperature control fruit.

Second embodiment: In this method, strains of Cryptococcus are selected that have the ability to control postharvest fruit pathogens. The test strain of Cryptococcus is grown up on a suitable nutrient medium. The cells are separated from the growth medium, e.g., by decanting, centrifugation, and washed to obtain cells substantially free of the growth medium. Next, the cells are suspending in water or buffer, to obtain a suspension having an effective amount of the organism, generally, about $1 \times 10^7$ CFU/ml. The suspension is applied to the surface or wound of the fruit, and the surface or wound is inoculated with the test pathogen in an amount sufficient to cause disease in fruit when compared to fruit treated identical to the test fruit except that no Cryptococcus treatment was applied (control). Similar to the first embodiment, the following amounts of pathogens are used for select a strain effective against the pathogen: at least $2 \times 10^4$ spores/ml Botrytis spp., $1 \times 10^4$ spores/ml Penicillium spp., or $4 \times 10^4$ to $1 \times 10^5$ spores/ml Mucor spp. The fruit is incubated for a sufficient time and at a temperature conducive to causing proliferation of the pathogen on the fruit.

Strains of Cryptococcus are selected which effectively inhibit the growth of the pathogen on the fruit. A strain is considered effective when it causes at least a 50% reduction in the number of fruit infected by the pathogen or at least a 50% reduction in the number of wounds infected by the pathogen, when compared to control fruit.

Growth of strains of the invention. Selected microorganism strains can be grown on any suitable solid or in liquid media. For example, for growth of yeast strains, solid media that can be used include nutrient-yeast extract-dextrose agar, V-8 agar, and malt extract agar. Growth of the strains are effected under aerobic conditions at any temperature satisfactory for growth of the organism, i.e., from about 0° C. to about 30° C.; the preferred temperature range is about 25° C. to 26° C. The pH of the nutrient medium is preferably about neutral, i.e., pH 6.7-7.2. The incubation time is that time necessary for the organism to reach a late log phase.

The strains may be grown in any conventional shake flask for fermentation runs, preferably at 26° C., at about 150-200 rpm in nutrient broth. For larger scale operations, it is convenient to carry out the culture in a fermentation tank, while applying agitation and aeration to the inoculated liquid medium. Following incubation, the organisms are harvested by conventional sedimentary methodology, e.g., centrifugation or filtering. The cultures are stored at about 4° C. until use.

Maintenance of stock cultures. Yeast cultures are maintained on NYDA (nutrient-yeast-extract-dextrose agar) composed of 20 g agar, 8 g nutrient broth, 4 g yeast extract, 1.5 g dextrose, 1 L deionized water. Additionally, cultures can be maintained for long term storage by lyophilization in 7% sterile skim milk.

Production of cultures. For production of yeast cells for biocontrol studies and screening procedures or for use to control disease, yeast cells are inoculated into an appropriate volume of growth medium, e.g., NYD broth (which is NYDA without the agar). The inoculated flask is incubated with agitation at about 26° C. for about 48 hours.

Uses of the strains of the invention. The strains are useful to control postharvest fruit pathogens. For purposes of the invention, control means that the incidence or severity of the disease is reduced or prevented, e.g., prevention of lesion development, reduction in lesion development, or reduction in lesion diameter compared to untreated fruit. In particular, the strains are useful to control disease caused by Mucor spp., Penicillium spp., and Botrytis spp. in fruit. For purposes of the invention, the term "fruit" is used herein in a botanical sense to mean the matured ovary with its seeds and any parts of the flower which may be closely associated with it. Exemplary of such fruit are pome fruit such as apples, pears, and quince; drupes such as cherries, peaches, and plums; berries; dry fruit such as legumes, e.g., sugar snap peas, and aggregate fruit such as strawberries.

The strains are preferably incorporated into compositions suitable for fruit application. They can be mixed with any agriculturally acceptable carrier such as water and buffer. Where the strain is applied as a suspension or emulsion in a liquid carrier, the suspension or emulsion may optionally contain conventional additives such as surfactants, wetting agents, and antioxidants. The organisms may also be applied in combination or concurrently with postharvest fruit fungicides.

The organisms are applied in an effective amount. For the purposes of this invention, an effective amount is defined as that quantity of microrganism cells sufficient to inhibit the development of the targeted fruit pathogen when applied to the fruit. Typically, a concentration range from about $1 \times 10^6$ to $1 \times 10^9$ colony forming units (CFU)/ml is effective. The preferred concentration range is from $1 \times 10^7$ to $1 \times 10^8$ CFU/ml. Factors such as ripeness of the fruit and concentration of the pathogen affecting the fruit will influence what quantity of organism cells is required to be effective. The amount that will be within an effective range can be readily determined by routine tests as described in Example 2, below.

The organisms of the invention may be applied to fruit using conventional methods such as drenching, dipping, or spraying. Application may be made immediately before harvest or preferably after harvest, prior to storage or shipment. For example, the organisms can be applied to harvested fruit while in bins, before being placed into storage, by drenching entire bins with suspensions of the organisms at an effective concentration, generally about $1 \times 10^8$ to $1 \times 10^9$ CFU/ml concentration using commercially-available bin drenchers, for example, drenchers that are presently used to drench fruit with fungicides. The organisms can be applied in water, physiological buffer, or in mixtures with postharvest label or lower rates of benzimidazole fungicides, e.g., thiabendazole, benomyl, to effectively control postharvest disease at the low temperatures at which fruit are stored commercially.

EXAMPLES

The following examples are intended only to further illustrate the invention and are not intended to limit the scope of the invention which is defined by the claims.

EXAMPLE 1

This example reports screening of 125 isolates of bacteria and yeasts for antagonistic activity against *Penicillium expansum, Penicillium viridicatum, Alternaria alternata, Botrytis cinerea,* and Mucor sp.

Isolation of Isolates. Orchards with minimal or no pesticide spray programs were preferentially, but not exclusively, selected for sampling. Leaves, flowers, stem tissue, and fruit collected from local apple, cherry, and pear orchards were placed in plastic bags on ice until returned to the laboratory. One-gram samples of leaf, stem, flowers, or fruit peels were placed in 10 ml sterile deionized water, vortexed briefly, evacuated by water aspiration for 20 minutes, then vortexed again. Serial dilutions of the water were plated onto nutrient-yeast extract-dextrose agar (NYDA; 20 g agar, 8 g nutrient broth, 4 g yeast extract, 1.5 g dextrose, 1 L deionized water) plates and incubated at 26° C. Colonies that differed in appearance on isolation plates were streaked onto nutrient agar to ensure purity, then stored in sterile deionized water at 4° C. until screened for biocontrol potential. If screening results were positive, the strain was then lyophilized for long term storage.

Screening of Isolates. Antagonists were evaluated by a modification of the final screening method used by Janisiewicz (*Phytopathology* 77: 481–485 (1987)) as follows: the bacteria and yeasts obtained as described above were grown for 48 hours in nutrient broth in an environmental shaker at 26° C. and 200 rpm. Cultures then were diluted with sterile deionized water to give suspensions of 0.5 $OD_{595nm}$ (about $10^7$–$10^9$ colony-forming units [cfu]/ml). Golden Delicious apple fruit were puncture-wounded (about 6.0 mm deep and 2.4 mm in diameter) three times each with a sterile, blunted, no. 13 stainless steel cannula, and 10 μl of a bacterial or yeast suspension was introduced into the wounds on each of five apples. After 30–60 minutes, 10 μl of sporangiospore suspensions of Mucor sp., or conidial suspensions of *A. alternata, P. expansum, P. viridicatum,* or *B. cinerea* at $2 \times 10^4$ spores/ml (as determined by hemacytometer) were introduced into the wounds of one fruit per pathogen. Positive controls consisted of wounded fruit that received pathogen spores but were not treated with potential antagonists. Wounded, water-treated fruit served as negative controls. Agent-alone controls were not used because of limitations on availability of fruit, and because production of lesions by a potential antagonist in screenings would itself indicate nonsuitability. Inoculated fruit were held on metal or plastic rings on wet paper toweling in closed polyethylene bins at 18° C. for 10 days, when lesion diameters were measured.

Source of fruit for bioassays. Apple fruit (cultivar Golden Delicious) used for bioassays of potential biocontrol agents and subsequent tests described in Examples 1-3 were harvested from trees at the Washington State University Tree Fruit Research and Extension Center, Wenatchee, Washington, or were purchased from commercial growers. Fruit were harvested at commercial maturity for controlled-atmosphere storage (starch index >2, firmness = 17–19 lbs) and run through a small-scale packing line. Packing operations included: immersion in dump tank water (pH 6.8–6.9) containing 3–5 g/ml chlorine dioxide (Rio Linda Chemical Co., Inc., Sacramento, CA) and 200 μg/ml Neodol 91-6, a non-ionic surfactant (North Coast Chemical Co., Inc., Seattle, WA); potable water rinse; hot drying at about 60° C.; and sizing. Sized fruit were packed in new 35-L (1 bushel) cardboard boxes and placed until use in a cold (0° C.) room or in a commercially operated room with controlled atmosphere ($O_2 = 1.5\%$, $CO_2 \leq 2\%$, 0°C.).

Statistical analysis. All experiments were repeated at least once. Homogeneity of variance for different trials of each experiment was evaluated by Hartley's F-Max test at $P = 0.05$ of the arcsine-square root transformation of the percentage of fruit that developed lesions. If variances did not differ significantly, data from separate trials were pooled, except for the effect of yeast concentration and temperature on biocontrol efficacy experiment. Pooled data was analyzed by analysis of variance, then means were separated by Waller-Duncan K-ratio t-test ($\alpha = 0.05$), or regression analysis in SAS (SAS Institute, Inc. 1987. SAS/STAT Guide for Personal Computers, Version 6 Edition. SAS Institute, Inc., Cary, NC. 1028 pp.) was performed as appropriate. Variances of trials from all experiments did not differ significantly, so data from all trials were pooled for each experiment prior to analysis.

Results. One yeast strain isolated from apple (*Malus sylvestris* Mill.) leaf tissue exhibited the greatest inhibition of gray mold lesion development by *B. cinerea* in initial screenings. The strain was identified as the obligately aerobic, basidiomycetous psychrophile *C. laurentii* NRRL Y-18623, and was selected for further study.

EXAMPLE 2

The following example reports studies of efficacy of *C. laurentii* NRRL Y-18623 in the control of the postharvest disease caused by *B. cinerea*, and effect of concentration and temperature on biocontrol efficacy.

Source of fruit. The apple fruit used for the tests were obtained as described in Example 1.

Treatment of fruit. Fruit from controlled-atmosphere storage were sorted by YID (yellow color values) determined by three averaged readings per fruit on a diode-array, tristimulus colorimeter (Pacific Scientific Co., Silver Spring, MD). Fruit with YID values from 68–74 were equatorially wounded once as described, and 10 μl of 0.5 $OD_{595nm}$ (about $1 \times 10^7$ CFU/ml) suspensions of washed cells of *C. laurentii* NRRL Y-18623 and conidial suspensions of *B. cinerea* at $2 \times 10^4$ conidia/ml were used. Both antagonist and pathogen suspensions were prepared in 0.05M phosphate buffer, pH 7.0. After 12 days of incubation, the percentage of fruit that developed lesions was recorded or maximum lesion diameters were measured after each fruit was sliced longitudinally through the wound. Slicing fruit before measurement permitted detection of occasional internal lesions that were not apparent by superficial examination, and prevented recording false negative data. Wounds inoculated with *C. laurentii* NRRL Y-18623 alone never developed lesions, so agent-alone controls were not used.

Statistical analysis. Statistical analysis was the same as described in Example 1, except that the larger sample size for the effect of concentration and temperature on biocontrol efficacy experiment precluded the need to pool data, so trials were analyzed separately.

Relative efficacy of *C. laurentii* and benomyl for gray mold control. Sets of 20 fruit were wounded, and either yeast suspensions in buffer (five fruit) or buffer alone (10 fruit) were introduced into the wounds. Five fruit per set were wounded, dipped in benomyl at the postharvest label rate (0.6 g/L, 50% a.i.), and allowed to air dry. After 30 minutes, conidia of *B. cinerea* were introduced into all wounds, except for the five that received only buffer and served as negative controls. Each treatment consisted of five single-fruit replicates in a randomized complete block design. Sets of 20 treated fruit were incubated 12 days in polyethylene moist chambers at 5, 10, 15, or 20° C., then evaluated for percentage of fruit with lesions.

Results. A positive relationship between temperature and the percentage of fruit that developed lesions was observed for fruit treated with *C. laurentii* NRRL Y-18623 ($r^2=0.89$) and for the inoculated control ($r^2=0.97$), but was absent in the benomyl-treated fruit ($r^2=0.10$, Table 3). Uninoculated control fruit did not develop lesions at any temperature. The percentage of wounds treated with *C. laurentii* NRRL Y-18623 that developed lesions did not differ from benomyl-treated wounds at 5, 15, and 20° C., but was significantly less than the benomyl treatment at 10° C. The percentage of fruit treated with *C. laurentii* NRRL Y-18623 that developed lesions was significantly less than in the inoculated buffer controls at all incubation temperatures. Similar reductions in percentage of fruit with lesions were observed in benomyl-treated fruit except at 10° C., where the percentage of fruit with lesions did not differ from the inoculated control.

TABLE 3

| Temp. °C. | Percentage of Fruit with Lesions[a] | | |
|---|---|---|---|
| | *C. laurentii* NRRL Y-18623 | Benomyl | Inoculated Buffer Control |
| 5 | 0.0 ± 0.0 d | 0.0 ± 0.0 d | 30.0 ± 30.0 c |
| 10 | 0.0 ± 0.0 d | 40.0 ± 0.0 bc | 40.0 ± 30.0 bc |
| 15 | 0.0 ± 0.0 d | 20.0 ± 0.0 d | 70.0 ± 30.0 b |
| 20 | 30.0 ± 0.0 c | 20.0 ± 0.0 bc | 100.0 ± 30.0 a |
| $r^{2b}$ | 0.89 | 0.10 | 0.97 |

[a]Means are averaged values of two trials ± the standard deviation. Values followed by the same letter are not significantly different at P = 0.05 according to analysis by Waller-Duncan K-ratio t-test of the arcsine-transformation of the percentage of fruit that developed lesions.
[b]Values are from linear regression analysis of the arcsine-square root transformation of the percentage of fruit that developed lesions. No lesions developed on the uninoculated buffer controls.

Effect of interval between wounding and inoculation with *B. cinerea*. Incubation temperature and the interval between wounding and inoculation with *B. cinerea* were varied to determine the effect on biocontrol with *C. laurentii*. Fifty fruit were wounded, then each wound was either treated with buffer or inoculated with *C. laurentii* NRRL Y-18623. Inoculations with *B. cinerea* were made at 0, 1, 24, 48, or 72 hours after wounding. After inoculation with *B. cinerea*, fruit were incubated in polyethylene moist chambers at 10 and 20° C. A single fruit served as one replicate in a randomized complete block design, with five replicates per set for each time and temperature combination.

Results. The percentage of fruit that developed lesions following inoculation with *B. cinerea* 0, 1, 24, 48 and 72 hours after wounding were 80.0±24.5, 50.0±10.0, 25.0±8.7, 5.0±8.7, and 0.0±0.0, respectively. The relationship of the percentage of fruit that developed lesions (Y) and the interval between wounding and inoculation (X) was described by Y=60.93−0.95(X), $r^2=0.72$. Wounds treated with *C. laurentii* at $10^5$ cfu/wound did not develop lesions after inoculation with *B. cinerea* after any interval between wounding and inoculation with *B. cinerea*.

Population studies of *C. laurentii* in wounds. The ability of *C. laurentii* NRRL Y-18623 cells to survive and multiply in wounds was studied to determine if *C. laurentii* is an effective colonizer of apple fruit wounds. Fruit were wounded, inoculated with washed cells of *C. laurentii* NRRL Y-18623 in buffer, and held in moist chambers at 5, 10, 15, or 20° C. Viable cell concentrations of the inoculum were determined by dilution plating onto NYDA. Individual fruit wounds served as one replicate in a randomized complete block design, and three replicates were sampled at each sampling time and temperature. Wounds were sampled 0 and 4 hours after inoculation, then every 24 hours until 96 hours had elapsed. Samples were taken by excising the entire wound from the apple with an ethanol-flamed, 6.7 mm (internal diameter) cork borer, trimming the resultant tissue cylinder to about 8 mm in length, and placing the sample in 10 ml sterile 0.05M phosphate buffer, pH 7.0. The tissue plug then was macerated with a glass rod, vortexed, dilution-plated in triplicate onto NYDA, and incubated at 26° C. for 3 days when colonies were counted. Population densities of *C. laurentii* were expressed as $\log_{10}$ CFU/wound.

Results. Population densities of *C. laurentii* NRRL Y-18623 in wounds increased with incubation time at all temperatures (FIG. 1). Although growth was more rapid at warmer temperatures, population densities of *C. laurentii* in wounds increased by approximately 2 log units over the initial population levels at all temperatures by 96 hours after inoculation. Regression analysis showed the relationship of the log of the mean number of cells per wound (Y) and hours of incubation (X) was: at 5° C., $\log Y = 4.62 + 0.0204(X)$, $r^2 = 0.99$; at 10° C., $\log Y = 4.77 + 0.0246(X) + 0.212(X^2)$, $r^2 = 0.98$; at 15° C., $\log Y = 4.94 + 0.0234(X) + 0.409(X^2)$, $r^2 = 1.0$; at 20° C., $\log Y = 5.08 + 0.0232(X) + 0.554(X^2)$, $r^2 = 0.97$. Repeated trials gave similar results.

Effect of temperature and concentration of *C. laurentii* on biocontrol efficacy. To determine the effect of cell concentration of *C. laurentii* NRRL Y-18623 on biocontrol efficacy, 0.5 OD$_{595nm}$ suspensions were serially diluted to $10^{-3}$, then 10 μl of each dilution was introduced into each of 10 wounded fruit, replicated four times per yeast concentration and temperature in a randomized complete block design. Wounds in control fruit received sterile buffer instead of yeast suspensions. Wounds were immediately challenged by inoculation with conidia of *B. cinerea*, then the fruit were sealed in polyethylene-lined 1 bu apple boxes and incubated at 5, 10, 15, or 20° C. for 12 days.

Results. As the incubation temperature decreased, the concentration of suspensions of *C. laurentii* NRRL Y-18623 necessary to prevent lesion development decreased (Table 4). The percentage of fruit that developed lesions decreased as either the incubation temperature decreased at each yeast concentration or the concentration of *C. laurentii* NRRL Y-18623 increased at each temperature.

TABLE 4

| $Log_{10}$ Y-18623 per wound | Temperature (°C.) | | | | $r^2$ |
|---|---|---|---|---|---|
| | 5 | 10 | 15 | 20 | |
| | Percentage of Fruit with Lesions[a] | | | | |
| 5.03 | 0.0 ± 0.0 | 5.0 ± 5.0 | 22.5 ± 8.3 | 45.0 ± 15.0 | 0.83 |
| 4.03 | 12.5 ± 0.0 | 42.5 ± 10.9 | 62.5 ± 10.9 | 77.5 ± 10.9 | 0.84 |
| 3.03 | 30.0 ± 7.1 | 55.0 ± 15.0 | 75.0 ± 11.2 | 100.0 ± 0.0 | 0.88 |
| 2.03 | 50.0 ± 18.7 | 85.0 ± 5.0 | 97.5 ± 4.3 | 100.0 ± 0.0 | 0.86 |
| C[b] | 42.5 ± 8.3 | 87.5 ± 8.3 | 97.5 ± 4.3 | 100.0 ± 0.0 | 0.88 |
| $r^2$ | 0.84 | 0.79 | 0.77 | 0.93 | |

[a]Percentages are actual values, $r^2$ values are from linear regression analysis of the arcsine-square root transformation of the percentage of fruit that developed lesions.
[b]Wounds in control fruit (C) received only buffer before inoculation with *B. cinerea*.

Mode of action. To determine if extracellular metabolites in culture broth were responsible for antagonism of *C. laurentii* against *B. cinerea*, *C. laurentii* NRRL Y-18623 was grown for 48 hours as described above, and cells and culture broth were separated by centrifugation. The supernatant was decanted, filtered through a 0.2 μm polycarbonate membrane filter, and reserved. Yeast pellets were washed three times with 45 ml 0.05M phosphate buffer, pH 7.0. Ten microliters of cell-free culture supernatant, suspensions of washed cells of *C. laurentii* in buffer, or buffer was introduced into each of five apple wounds in a randomized complete block design. After 30 minutes, conidia of *B. cinerea* were introduced into each wound, and the fruit was incubated for 12 days in polyethylene moist chambers at 20° C.

Results. Wounds treated with triple-washed cells of *C. laurentii* NRRL Y-18623 did not develop lesions after inoculation with *B. cinerea*. Wounds treated with cell-free culture broth of *C. laurentii* developed rapidly expanding lesions (62.5±11.9 mm in diameter) after inoculation with *B. cinerea*. Lesions that developed from wounds treated only with buffer before inoculation with *B. cinerea* were significantly (P=0.05) smaller (33.8±20.8 mm in diameter) than those from wounds treated with culture broth. All culture broth- or buffer-treated fruit developed lesions after inoculation with *B. cinerea*.

Summary of results. When wounds on apple fruit were pretreated with the Cryptococcus strain, development of lesions of *B. cinerea* was effectively reduced or prevented. No necrosis or darkening of fruit tissue was associated with any concentration of the strain in wounds. The level of control of lesion development of *B. cinerea* by the strain compared very favorably with levels observed in benomyl-treated fruit and was accomplished without apparent antibiosis by extracellular metabolites characteristic of certain postharvest biocontrol agents.

The reduction in percentage of fruit that developed lesions by postharvest application of Cryptococcus to wounded apple fruit was very great (55-100%). The rapid growth of the Cryptococcus strain in wounds over a wide range of temperatures, especially cold temperatures, and its ability to control lesion development by Botrytis provides evidence that the Cryptococcus strain is well adapted to the wound environment in apple fruit. Although the growth of the strain in wounds was more rapid at warmer temperatures, its ability to multiply in wounds at 5° C. is significant because of the low temperature at which fruit commonly are stored.

EXAMPLE 3

Unwounded Bing cherry fruit were treated after harvest by immersion for 1 minute in tap water (control) or in a suspension of *C. laurentii* Y-18623 ($1 \times 10^7$ CFU/ml). Each control and yeast treatment consisted of 100 fruit replicated four times. The entire experiment was repeated once. The fruit were stored for 11 days at 5° C. and subsequently for 11 days at 15° C.

Results. The percentage of treated cherries infected by a postharvest fungus after 22 days storage was reduced an average of 20-25% compared to the controls. This compared favorably with treatment with a bleach solution that was five times stronger than that used for commercial control of fungi.

EXAMPLE 4

The following example describes a screening procedure developed to screen microrganisms strains for potential for control of fungi-induced postharvest fruit rots.

Screening of isolates. The isolates were grown in nutrient broth (Bacto beef extract 3 g/L and Bacto peptone 5 g/L). After 48 hours, the broth cultures were decanted into sterile 50-ml centrifuge tubes and centrifuged at 2,500 rpm for 3 minutes, and the supernatant discarded. The pellet was washed by resuspension in sterile 0.05M phosphate buffer, pH 7.0, vortexing, and recentrifuging. The cells were washed twice in this manner, then the yeast pellet was resuspended in sterile buffer so that the cell suspension gave about 50% transmission at 560 nm. This corresponds to a cell concentration of about $1 \times 10^7$ cells per ml.

Pathogen spore suspensions for use in biocontrol studies or screening assays were prepared as follows. *Penicillium expansum* was grown for 7-11 days at 18° C. on half-strength V8 juice agar. Mucor sp. was grown for 7-14 days at 15° C. on potato dextrose agar at 18° C. under alternating UV/fluorescent light (15 hours) and dark (9 hours) conditions. Spores were harvested from agar plates and suspended in sterile buffer at $2 \times 10^4$ spores/ml (*Botrytis cinerea* and *Penicillium expansum*) or $4 \times 10^4$ to $1 \times 10^5$ spores/ml (Mucor).

Pear and apple fruit were surface-disinfested by swabbing with 70% ethanol or immersion in 100 ppm sodium hypochlorite for 2 minutes. Individual fruit were puncture-wounded (about 6.0 mm deep and 2.4 mm in diameter) three times each with a sterile, blunted, no. 13 stainless steel cannula, and 10 μl of yeast suspension was introduced into the wounds on each of four apples or pears. After 30 minutes, 10 μl of pathogen spore suspension of Mucor sp., *P. expansum*, or *B. cinerea* were introduced into each wound on four apples or pears. This resulted in the evaluation of biocontrol of each pathogen in 12 wounds per yeast strain. Control fruit received buffer in their wounds, then the pathogen spores, but no yeast cells.

Inoculated fruit were held in moist chambers at 20° C. (for *Penicillium expansum* and *Botrytis cinerea*) or 15° C. (for Mucor) for 5-14 days. When large lesions (greater than about 30 mm) were present on control fruit, the other fruit treated with yeast were evaluated for biocontrol by radially slicing each wound through the fruit, then measuring the maximum lesion diameter. Data on lesion diameters and number of lesions that developed decay was recorded and compared to corresponding data from control fruit. When tested on apples, strains that gave a ≧65% reduction in number of wounds with lesions from Mucor sp. compared to controls, ≧80% reduction in number of wounds with lesions from *B. cinerea* compared to controls, or ≧50% reduction in number of wounds with lesions from *P. expansum* compared to controls, were considered potential biocontrol agents for control of a target postharvest fruit rot. Cryptococcus strains NRRL Y-18617, NRRL Y-18618, NRRL Y-18619, NRRL Y-18620, NRRL Y-18621, and NRRL Y-18622 met the criterium for each target fungus.

EXAMPLE 5

Pears were used that had been in cold storage since harvest, but because of a malfunction in the cold room refrigeration equipments, had gotten warm and had become ripe.

*C. laurentii* strain NRRL Y-18622, *C. flavus* strains NRRL Y-18617, Y-18618, Y-18619, and Y-18620, and *C. albidus* strain NRRL Y-18621 were grown for 48 hours in nutrient-yeast extract-dextrose broth at 26° C. and 200 rpm, harvested, and washed (3 times) by centrifugation and resuspension in 0.05M phosphate buffer, 7.0. All suspensions were then adjusted to approximately 2% light transmittance at 560 nm (about $1 \times 10^8$ CFU/ml). Mucor conidia were harvested by scraping from 12 day-old potato dextrose agar cultures grown at 15° C., suspended in phosphate buffer (as above), and the concentration adjusted to $1 \times 10^5$ cfu/ml using a hemocytometer. Each yeast strain and the pathogen controls were tested in 120 surface-disinfected pear fruit that were puncture-wounded 2.4 mm wide ×6.0 mm deep. Ten µl of a cells suspension of a given yeast was introduced into the wounds in 120 fruit. Pathogen controls received sterile buffer at this step, but no yeast cells. After no longer than 10 minutes, 10 µl of the Mucor spore suspension were introduced into the wounds in all fruit. The sets of 120 pears were then subdivided into groups of 10 pears, which allowed for 4 replicates of 10 pears for each incubation temperature (15, 10, 5° C.) for each yeast strain. Pears were stored on fiber trays in 1 bushel cardboard boxes at the respective temperatures with 1 replicate of each yeast strain and 1 replicate of the pathogen control present in each box. Disease development and control was evaluated after 5 days for 15° C. fruit, after 7 days for 10° C. fruit, and 12 days for 5° C. fruit. Each wound was evaluated for the presence of a Mucor lesion after the wound was sliced to reveal any internal lesion development that could have been missed with just superficial examination.

Figure 2:
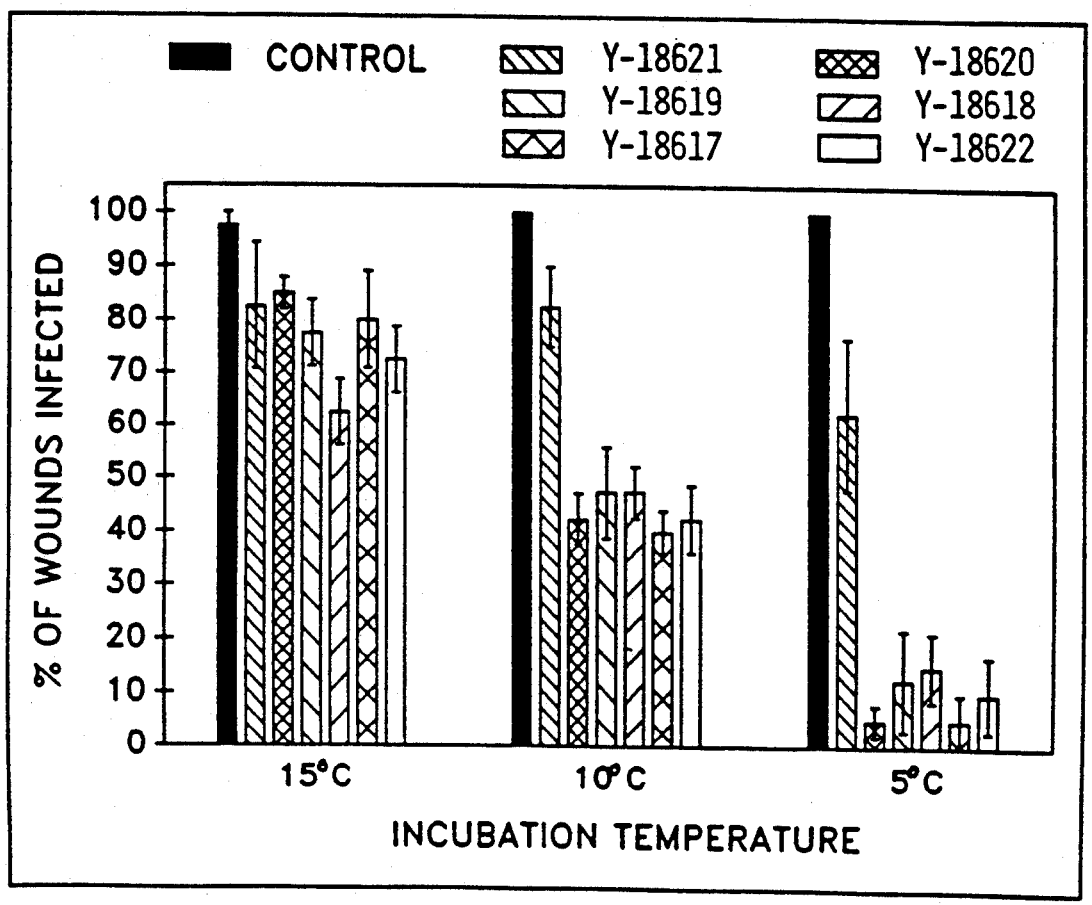
FIG. 2 shows biocontrol data for Mucor rot of ripe pears at three storage temperatures with strains of Cryptococcus. Bars represent the standard error of the mean.

FIG. 2 shows the percent of wounds that became infected (had a lesion present at the wound site). As can be seen from the figure, as the storage temperature decreased, biological control increased, demonstrating the effectiveness of these strains in cold storage.

EXAMPLE 6

Pears were used that had been in commercial cold storage (about 1°-2° C.) since harvest, and were not subjected to ripening conditions as had the pears described in Example 5. Fruit held at 15° C. were evaluated after 7 days storage; those held at 10° C. were evaluated after 13 days storage, and those held at 5° C. were evaluated after 20 days storage. The other materials and methods were as described in Example 5.

Figure 3:
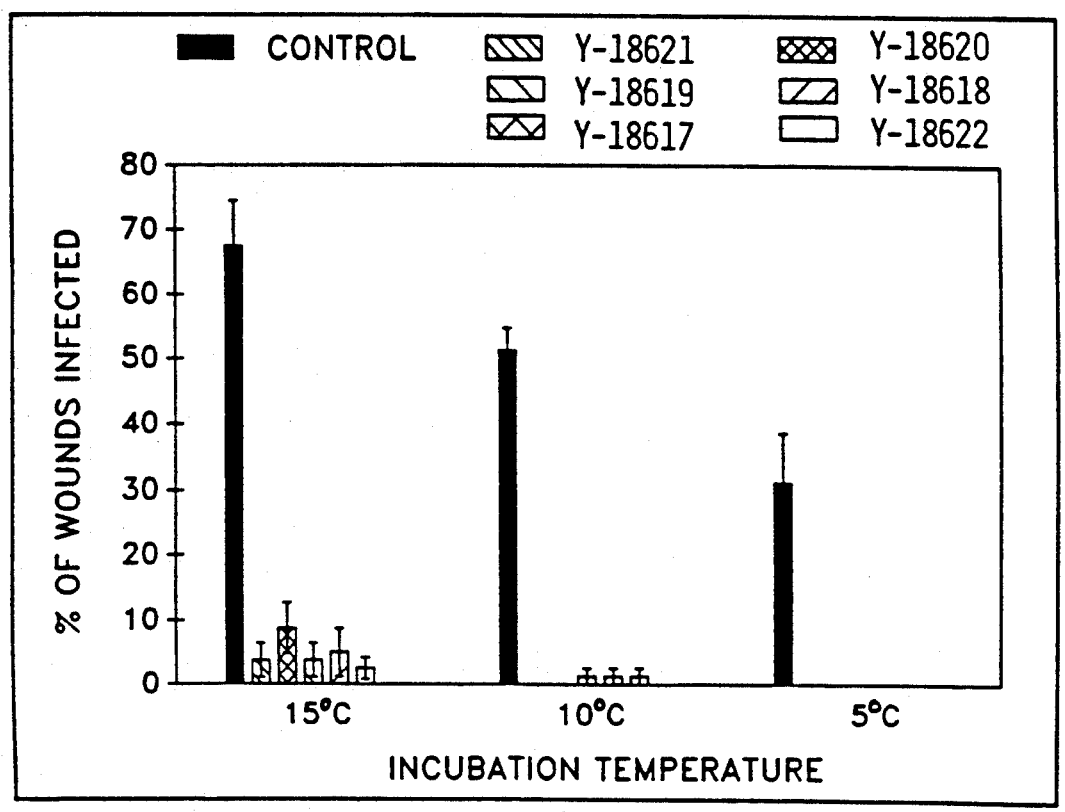
FIG. 3 shows biocontrol data for Mucor rot of unripe pears at three storage temperatures with strains of Cryptococcus. Bars represent the standard error of the mean.

Data for the unripe pear trial is presented in FIG. 3. As shown by the data, biocontrol efficacy is greatly enhanced when the yeast is used on unripe fruit, which is comparable to normal treatment procedure of application just after harvest. Prevention of any lesion development was very great. The absence of a vertical bar indicates 100% control.

EXAMPLE 7

The following experiment tests the compatibility of the strains with other postharvest chemicals. Cryptococcus strains NRRL Y-18617, NRRL Y-18618, NRRL Y-18619, NRRL Y-18620, NRRL Y-18621, NRRL Y-18622, and NRRL Y-18623 were tested in vitro for growth in the presence of the following fungicides at 500 ppm active ingredient: benomyl, thiabendazole, iprodione, and sodium orthophenylphenate (SOPP). Growth was also tested in the presence of 2000 ppm of the antioxidant, diphenylamine.

None of the test chemicals inhibited growth of any of the strains. This demonstrates the compatibility with other postharvest treatments.

It is understood that the foregoing detailed description is given merely by way of illustration and that modification and variations may be made within without departing from the spirit and scope of the invention.

Having thus described my invention, I claim:

1. A method for biologically controlling disease in fruit caused by a postharvest wound or surface fruit pathogen, comprising subjecting a fruit to a strain of Cryptococcus yeast in an amount effective to inhibit the development of said pathogen, wherein said strain is characterized by the property of causing at least a 50% reduction in the number of fruit infected by said pathogen, or at least a 50% reduction in the number of wounds infected by said pathogen, when compared to fruit contacted with said pathogen in the absence of said strain.

2. The method of claim 1 wherein said strain is selected from the group consisting of *Cryptococcus flavus* NRRL Y-18617, *Cryptococcus flavus* NRRL Y-18618, *Cryptococcus flavus* NRRL Y-18619, *Cryptococcus flavus* NRRL 18620, *Cryptococcus albidus* NRRL Y-18621, *Cryptococcus laurentii* NRRL Y-18622 and *Cryptococcus laurentii* NRRL Y-18623.

3. The method of claim 1 wherein said postharvest fruit pathogen is selected from the group consisting of Botrytis spp., Penicillium spp., and Mucor spp.

* * * * *